United States Patent [19]

Bartell

[11] Patent Number: 4,681,102
[45] Date of Patent: Jul. 21, 1987

[54] APPARATUS AND METHOD FOR INSERTION OF AN INTRA-OCULAR LENS

[76] Inventor: Michael T. Bartell, 2867 Mill Rd., Doylestown, Pa. 18901

[21] Appl. No.: 774,720

[22] Filed: Sep. 11, 1985

[51] Int. Cl.[4] .......................... A61F 2/16; A61B 17/00
[52] U.S. Cl. ..................................... 128/303 R; 623/6
[58] Field of Search ............ 623/6; 128/303 A, 303 R

[56] References Cited

U.S. PATENT DOCUMENTS

| | | |
|---|---|---|
| 4,122,556 | 10/1978 | Poler . |
| 4,198,980 | 4/1980 | Clark . |
| 4,214,585 | 7/1980 | Bailey . |
| 4,244,370 | 1/1981 | Furlow ........................... 128/303 R |
| 4,249,271 | 2/1981 | Poler . |
| 4,251,887 | 2/1981 | Anis . |
| 4,253,199 | 3/1981 | Banko . |
| 4,257,521 | 3/1981 | Poler . |
| 4,298,994 | 11/1981 | Clayman . |
| 4,349,027 | 9/1982 | DiFrancesco . |
| 4,423,809 | 1/1984 | Mazzocco . |
| 4,446,581 | 5/1984 | Blake . |
| 4,449,257 | 5/1984 | Koeniger . |
| 4,463,457 | 8/1984 | Kelman . |
| 4,468,820 | 9/1984 | Uhler . |
| 4,490,860 | 1/1985 | Rainin . |
| 4,573,998 | 3/1986 | Mazzocco ...................... 128/303 R |

OTHER PUBLICATIONS

IOL & Ocular Surgery News, vol. 1, No. 14, 7/15/83.

Primary Examiner—Carlton R. Croyle
Assistant Examiner—T. Olds
Attorney, Agent, or Firm—William H. Eilberg

[57] ABSTRACT

An apparatus and method for inserting an intra-ocular lens into an eye is disclosed. The apparatus permits the insertion of the intra-ocular lens through small incisions, of the order of several millimeters, such as are employed in the phacoemulsification technique of cataract removal. The intra-ocular lens is placed within a hinged, generally cylindrical load chamber, having a pair of flanges. The load chamber is folded around the intra-ocular lens, so that the lens itself becomes folded or rolled along its length. The load chamber is fitted into an injector portion, which has a slot which is keyed to the flanges of the load chamber. The injector portion and load chamber are then fitted into an insertion cone which defines a lumen for passage of the intra-ocular lens through the lumen. A plunger inserted into the injector portion is used to push the intra-ocular lens through the lumen and into the eye. The folded intra-ocular lens gradually flowers out as it emerges from the distal end of the insertion cone.

36 Claims, 10 Drawing Figures

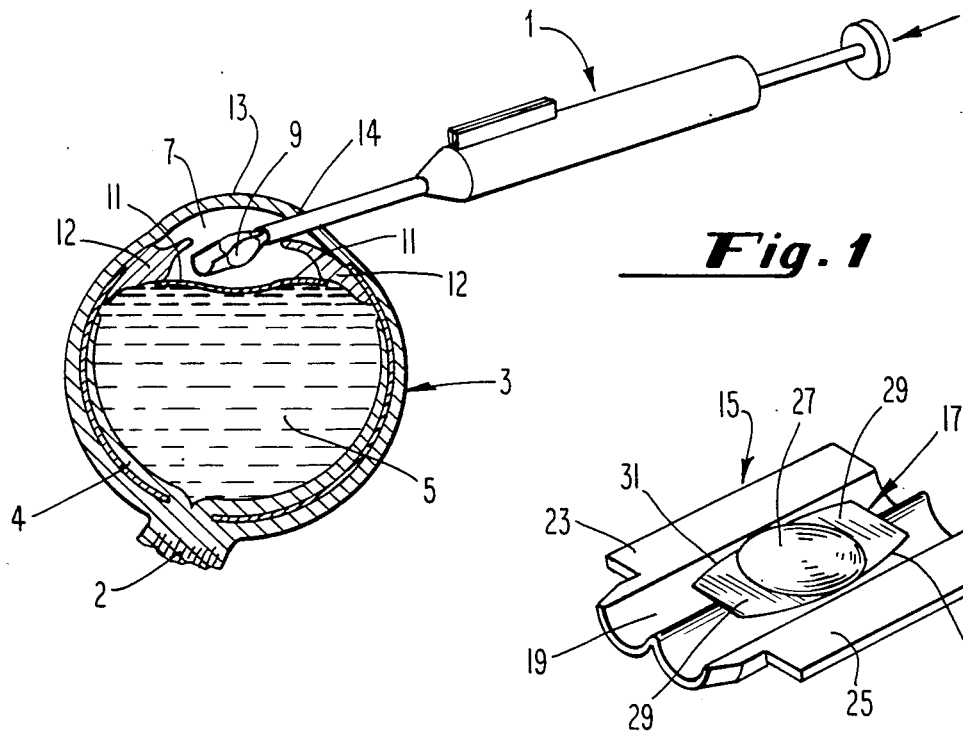
*Fig. 1*
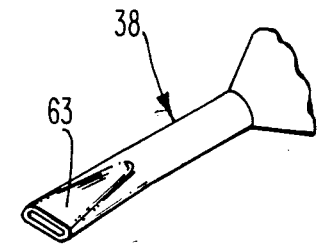
*Fig. 3A*
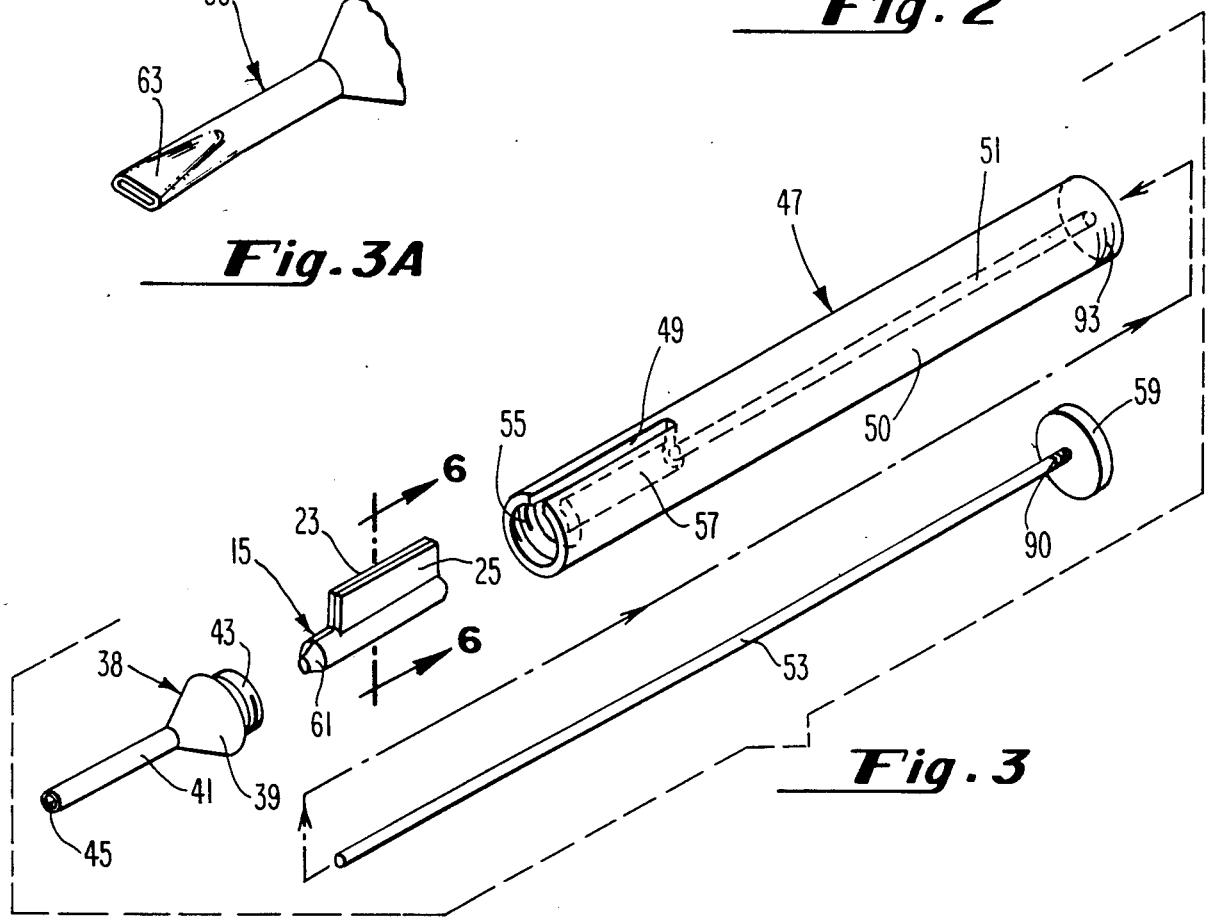
*Fig. 2*
*Fig. 3*

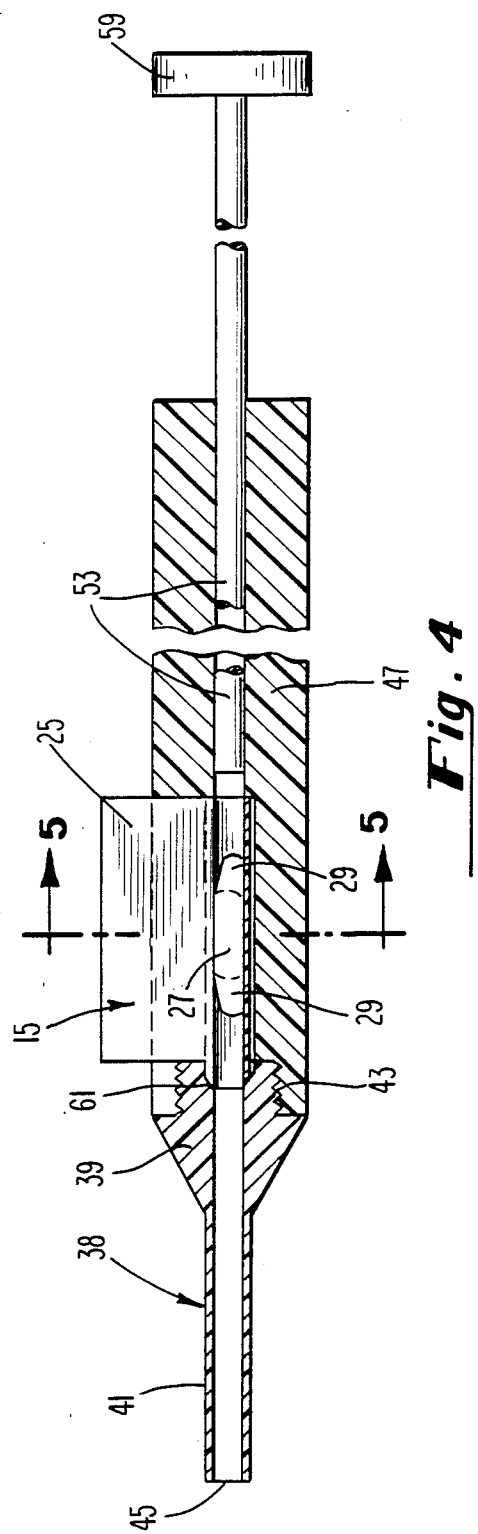
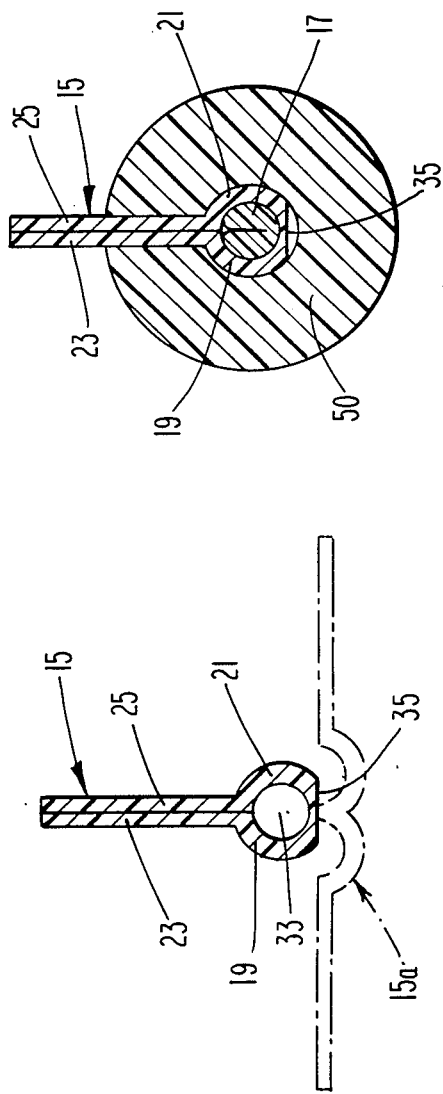
Fig. 4
Fig. 5
Fig. 6

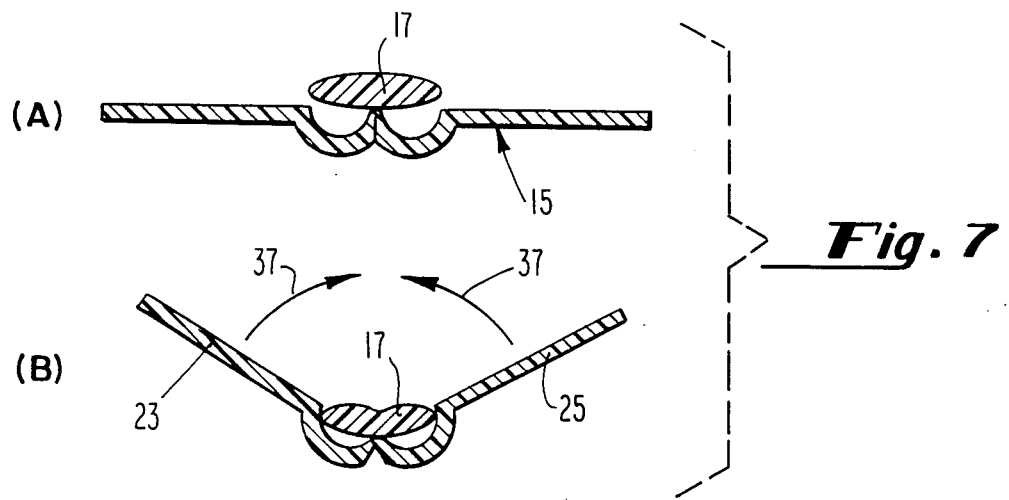
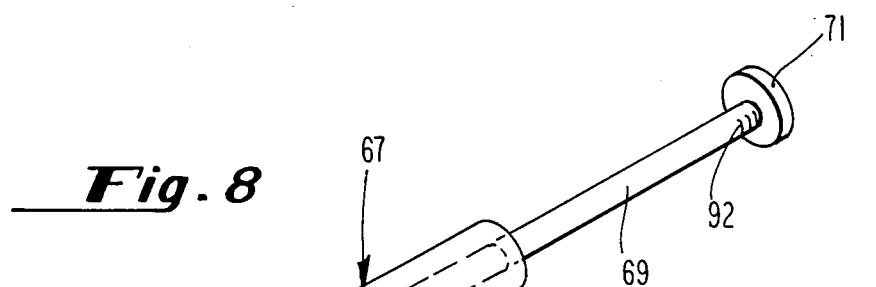
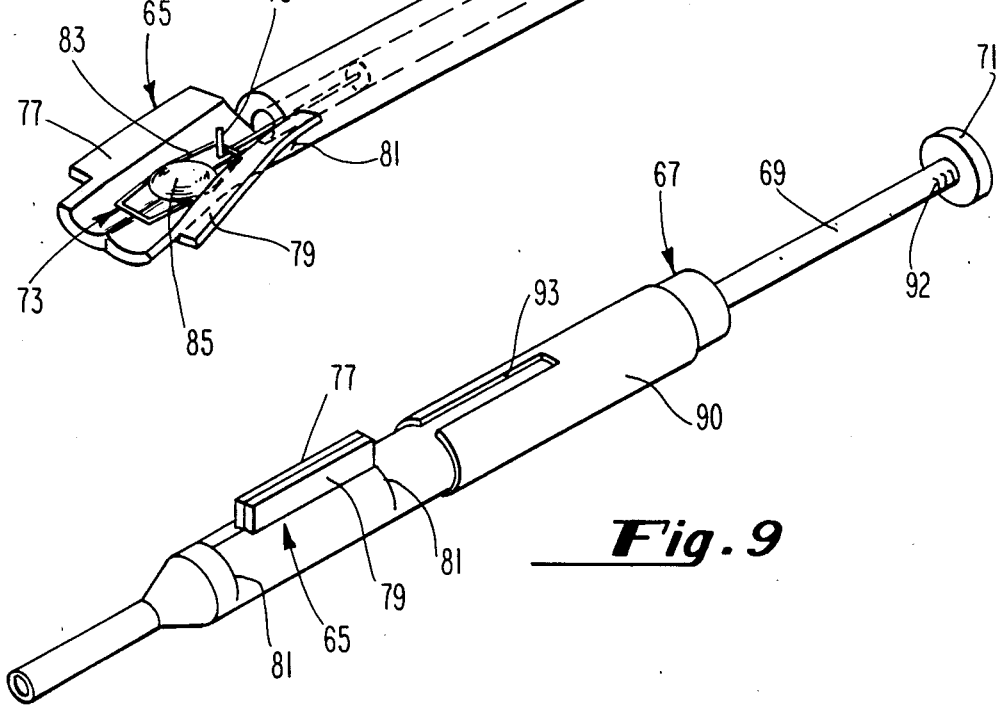

APPARATUS AND METHOD FOR INSERTION OF AN INTRA-OCULAR LENS

BACKGROUND OF THE INVENTION

The present invention relates to the field of cataract surgery, and, more particularly, to the insertion of an artificial intra-ocular lens into the eye, following such surgery.

A cataract is a clouding of the natural lens, the part of the eye located behind the cornea, and behind the aqueous humor. The natural lens is encapsulated within a membrane, the posterior portion of which forms a boundary between the aqueous and vitreous humors. The lens focuses light on the retina, on the rear wall of the eye, for transmission to the brain. When the clouding of the natural lens become severe, the patient can no longer see through that eye, and the cataract must be removed.

Various procedures have been known in the field of cataract removal. The earliest techniques required a large incision in the cornea. In the so-called intra-capsular procedures, so designated because they involved removing the entire natural lense and membrane encapsulating the lens, it was necessary to make an incision extending along a 180° arc around the cornea. The natural lenses would then be extracted, by cryogenic freezing and surgical removal, or by other means. The large incision needed to perform this surgery increased the risk, discomfort, and convalescence time associated with the operation.

Eventually, other techniques were developed which reduced the size of the incision necessary for removal of the cataract. In the so-called extra-capsular procedure, an incision of the order of 11-13 mm was made in the cornea, and the hard nucleus of the cataract was forced out of, or "expressed" from, the eye by gentle application of pressure. With this procedure, it became possible to preserve the posterior portion of the soft membrane, thereby maintain a separation between the aqueous and vitreous humors.

The procedures requiring an 11-13 mm incision were an improvement over the older techniques, but still engendered a certain amount of discomfort and risk. Eventually, a new technique for cataract removal, known as phacoemulsification, was developed. In this procedure, a hollow, vibrating needle and infusion sleeve are inserted into a small incision in the eye, the incision being only about 3 mm long. The needle vibrates at an ultrasonic rate, and the vibration causes the cataracted natural lens to be emulsified into tiny pieces. The remains of the natural lens are then drawn out by suction.

Removal of the clouded natural lens is only half of the solution for a cataract patient. The natural lens serves a vital purpose, namely the focusing of images of the retina. The natural lens has a refractive power of the order of about 19 diopters, so a person whose natura lens has been removed needs a powerful artificial lens to compensate for the missing lens. In the past, it was necessary for cataract surgery patients to be obliged to wear extremely thick eyeglasses for the rest of their lives.

Dissatisfaction with the use of these thick eyeglasses led to a search for an artifical intra-ocular lens (IOL), which could substitute for the natural lens. Many varieties of IOLs, and methods for their insertion and storage, were devised. Examples of IOLs in the patent literature are given in U.S. Pat. Nos. 4,122,556, 4,249,271, 4,251,887, 4,253,199, 4,298,994, 4,446,581, 4,449,257, 4,463,457, 4,468,820, and 4,490,860. Other references dealing with insertion methods for IOLs are U.S. Pat. Nos. 4,198,980, 4,214,585, and 4,349,027. U.S. Pat. Nos. 4,423,809 and 4,257,521 deal with packaging systems for IOLs.

The phacoemulsification process is very advantageous because of the extremely small incision required. But this advantage has, in the past, been surrendered when the time comes for insertion of an IOL Most IOLs require incisions having a length of about 6.5-8.0 mm, which means that the 3 mm incision made to perform the phacoemulsification needs to be enlarged by a factor of at least 2. It has therefore been necessary to enlarge the wound made during the cataract removal operation, before inserting the IOL.

The above-described problem has been partially solved with the introduction of flexible IOLs. Such IOLs are described in an article in IOL & Ocular Surgery News, Vol. 1, No. 14 (July 15, 1983), entitled "News Lens Allows Insertion in 3 mm Wound". The IOL is constructed of silicone, and can be folded, so that it can be inserted into a 3 mm incision.

Despite the introduction of flexible IOLs, there is still lacking a reliable and simple method of inserting such a lens. The present invention solves this problem, by providing an apparatus and method for IOL insertion, which is relativey easy to perform, and which requires no larger incision in the eye than that required for the phacoemulsification process. In short, the present invention makes it possible to exploit fully the advantages of phacoemulsification, by providing a simple, safe, and minimally traumatic means of inserting a flexible intra-ocular lens.

SUMMARY OF THE INVENTION

The apparatus of the present invention comprises three main components. The first component is a load chamber, which is a hinged structure for holding the IOL to be inserted into the eye. The load chamber can be folded, around its hinged portion, to define a lumen through which the IOL can pass. The second component is an insertion cone, next to which the load chamber abuts. The insertion cone has a bore which forms a continuation of the lumen defined by the load chamber. The insertion cone terminates, at its distal end, in a narrow tip, which is inserted through the small incision in the eye. The IOL is advanced through this tip and into the eyes. The third component is an injector portion, which fits over the load chamber, and attaches to the insertion cone. The injector portion is equipped with a plunger device which advances the IOL through the continuous lumen, and into the eyes.

According to the method of the present invention, the load chamber is laid out in its fully open position, and the IOL is laid upon the central portion of the opened load chamber. The load chamber, which preferably has a pair of flanges to assist in grasping and folding, is folded over to form a generally cylindrical lumen containing the IOL. When the load chamber is so folded, the IOL is rolled within its lumen. The effective width if the IOL is therefore reduced by more than half.

The folded load chamber is then inserted into the distal end of the injector portion. Then the insertion cone is threaded into the injector portion and tightened, causing the abutment and alignment of all inner lumens.

The injector portion is provided with a slot which is keyed to the flanges in the load chamber, thereby retaining the load chamber rigidly in place within the injector portion, and assuring the orientation of the lens. The proximal end of the insertion cone has a threaded member which engages the injector portion.

A plunger, inserted into the injector portion, is advanced through the lumen defined by the injector portion, the load chamber, and the insertion cone, until the IOL reaches the distal tip of the insertion cone. The apparatus is inserted through the incision in the eye, and the IOL is then inserted into the eye by pushing the plunger still further. As the IOL exits at the distal tip of the insertion cone, it "flowers out" gradually, regaining its original configuration. The physician can then adjust the final position of the IOL with a thin needle, or other similar instrument, inserted through the incision.

In another embodiment, suitable for use with IOLs having looped haptics without webbing, the injector portion and the load chamber are connected. The plunger is provided with a blunt hook at its distal end. The plunger is first advanced through the injector portion and into the load chamber, and the IOL is then laid onto the load chamber, such that its haptic overlies, and is engaged by, the hook. The load chamber is folded and attached to the insertion cone. When the plunger is advanced further, its distal end will push against the optic of the IOL, and not against the haptic. This embodiment prevents the plunger from damaging the haptic, when the haptic is of less sturdy construction.

It is therefore an object of the invention to provide a apparatus and method for inserting an intra-ocular lens (IOL) into an eye.

It is another object of the invention to provide an apparatus and method as described above, wherein the IOL can be inserted through a very small incision.

It is another object of the invention to provide an apparatus and method as described above, wherein the advantage of the small size of the incision made during a phacoemulsification process, or other surgical process, are fully exploited.

It is another object of the invention to provide an apparatus and method as described above, wherein the apparatus is simple to use, and wherein the apparatus minimizes the amount of handling of the IOL during insertion into the eye.

It is another object of the invention to provide a load chamber for an IOL, which facilitates the loading of an IOL into an insertion mechanism, and which also can be used to store the IOL temporarily.

It is another object to provide a method and apparatus for inserting an IOL, which can be used with IOLs having haptics which are simple loops.

Other objects and advantages of the invention will be apparent to those skilled in the art, from a reading of the following brief description, of the drawings, the detailed description of the invention, and the appended claims.

BRIEF DESCRIPTION OF THE DRAWINGS

FIG. 1 is a diagrammatic view showing an intra-ocular lens being inserted into an eye, according to the present invention.

FIG. 2 is a perspective view of an intra-ocular len, lying upon an opened load chamber.

FIG. 3 is an exploded perspective view showing the insertion cone, the load chamber, and the injector portion, including the plunger, for inserting the intra-ocular lens into the eye.

FIG. 3A is a perspective view of the distal end of the insertion cone, showing a flattened distal tip.

FIG. 4 is a cross-sectional view of the assembled apparatus for inserting an intra-ocular lens into the eye.

FIG. 5 is a cross-sectional view, taken along the line 5—5 of FIG. 4.

FIG. 6 is a cross-sectional view of the load chamber, taken along the line 6—6 of FIG. 3, and also showing, in phantom, the load chamber in the open position.

FIG. 7 is a cross-sectional view of the load chamber and the intra-ocular lens, showing the folding of the lens within the load chamber.

FIG. 8 is a perspective view of an alternative embodiment of the invention, wherein the load chamber is connected to the injector portion, and showing the load chamber in the open position.

FIG. 9 is a perspective view of the another embodiment, wherein the load chamber, the injector portion, and the insertion cone are formed of one piece, and showing the load chamber in the closed position.

DETAILED DESCRIPTION OF THE INVENTION

An overview of the apparatus of the present invention is shown in FIG. 1. Insertion apparatus 1 is shown injecting the artificial intra-ocular lens (IOL) 9 into eye 3. The eye 3 has a membrane 11, which separates the the aqueous humor 7 from the vitreous humor 5. The IOL is shown being pushed, or "expressed", out of the insertion apparatus 1, into the area formerly occupied by the natural lens of the eye (not shown in FIG. 1). FIG. 1 shows the cornea, which is at the front of the eye, as indicated by reference numeral 13, the ciliary bodies 12, and the iris 14, through which the apparatus 1 may be inserted. Also shown in FIG. 1 is the retina 4 and the optic nerve 2.

The intra-ocular lens (IOL), to be inserted according to the present invention, is illustrated in the perspective view of FIG. 2, which also shows an opened load chamber 15 according to the invention. The IOL, designated generally by reference numeral 17, is shown, in FIG. 2, lying on the opened load chamber. The load chamber, which is preferably constructed of a flexible plastic material, has a pair of generally semi-cylindrical members 19 and 21, and a pair of flanges 23 and 25 attached to those members. The flanges are sufficiently wide to facilitate grasping of the folded load chamber by the fingers. The semi-cylindrical members together define a "living hinge", i.e. a hinge which permits the load chamber to be opened fully, as shown in FIG. 2, but which also permits the load chamber to close to form a lumen for the IOL.

It is preferable that load chamber 15 be constructed in one piece, but it is possible to construct the flanges as separate elments and to attach them to the semi-cylindrical members.

IOL 17 comprises an optic portion 27 and a pair of haptic portions 29. Optic portion 27 comprises the substitute for the natural lens, i.e. it is the actual lens which can properly focus light entering the eye onto the retina. The haptics 29 comprise a pair of webbed portions, and are used for anchoring the IOL in its proper position. In an alternative embodiment, to the described later, the invention can also be used with IOLs having haptics which are not webbed, but which take the form of simple loops.

The folding of the load chamber, and of the IOL itself, is illustrated in the cross-sectional views of the FIGS. 6 and 7. FIG. 6 shows load chamber 15 in the folded position, and also shows a phantom drawing of the load chamber in the open position, as designated by reference numeral 15a. Members 19 and 21 together define a generally cylindrical lumen 33, in which the IOL can fit. The bottom portions of members 19 and 21 are flattened at the position indicated by reference numeral 35, permitting the load chamber to open fully, as shown in the phantom drawing.

The placement of the IOL into the load chamber is further illustrated in FIG. 7. FIG. 7A shows the IOL 17 which has been laid on the opened load chamber 15. FIG. 7B shows the load chamber being folded, with the aid of flanges 23 and 25, in the direction shown by arrows 37. Since the IOL is laid on the load chamber along its length, as shown in FIG. 2, the IOL will be folded, or rolled, along its length, when the load chamber is itself folded.

The exploded perspective view of FIG. 3 shows the components of the apparatus of the present invention. Load chamber 15 is shown in its folded orientation, and the load chamber is assumed to have a folded IOL inside. Also visible in FIG. 3 is insertion cone 38. The insertion cone has a generally conical portion 39, a cylindrical distal end portion 41, and a threaded cylindrical projection 43, located at the proximal end of the insertion cone. The term "distal" end, as used herein, means the end which enters the body first, i.e. the end which is more distant from the physician. In FIG. 3, it is distal tip 45 which first enters the eye. The term "proximal" refers to the end which is closer to the physician.

The conical shape of portion 39 of the insertion cone facilitates gripping of the insertion cone, and also makes it easier to insert the apparatus into the eye. However, it is also possible to replace the conical portion with a squared-off portion, within the scope of the invention.

The distal end portion of the load chamber is beveled, as is indicated by reference numeral 61. The bevel enhances the mating of the load chamber with the interior of the insertion cone.

FIG. 3 also shows injector portion 47, which is a generally cylindrical structure. The injector portion has a generally cylindrical body 50, the body having a slot 49 which is constructed to receive flanges 23 and 25 of load chamber 15. The injector portion also has a large bore 57, which can accommodate the load chamber 15, and a smaller bore 51, into which plunger 53, having handle 59, can be inserted. The injector portion is also provided with threads 55, on the interior wall of bore 57, for engagement of the injector portion with the insertion cone. When the injector portion is screwed onto the insertion cone, the lumens of the injector portion and insertion cone become precisely aligned.

The proximal end of the plunger, and the interior of the proximal end of the injector portion can also be threaded, as indicated by reference numerals 90 and 93, so that the plunger can be screwed into the injector portion when the apparatus is not in use.

FIG. 4 illustrates, in cross-section, the entire apparatus in assembled form. The figure shows insertion cone 38, including its distal end portion 41, its distal tip 45, its conical portion 39, and the threaded cylindrical portion 43. Load chamber 15 is also shown, with flange 25 being visible in the figure. The flanges are of sufficient width to extend beyond the boundary of the injector portion. The flanges can therefore be grasped even when the load chamber is fitted within the injector portion.

The bevel 61 on the end of the load chamber is shown in abutment with a corresponding surface of the interior of threaded cylindrical portion 43. The optic 27 and haptics 29 of the IOL are visible in the center of the figure. The load chamber is enclosed within injector portion 47. The figure also shows the plunger 53 and handle 59 of the injector portion.

FIG. 5, a cross-sectional view taken along the line 5—5 of FIG. 4, further illustrates the IOL in its folded position. The figure shows body 50 of the injector portion, flanges 23 and 25 and cylindrical members 19 and 21, of load chamber 15. Also visible is IOL 17. Flattened portion 35 of the load chamber is also shown.

The lumen defined by the load chamber is preferably treated with a lubricating material, such as the substance known by the trade name of Healon, or any other suitable lubricant. This treatment will facilitate the passage of the IOL through the lumen, without damage to the IOL. It is also possible to provide a lubricant of sufficient viscosity, and in sufficient quantity, to form a plug between the tip of the plunger and the IOL. In the latter case, the plunger will not contact the IOL, and therefore cannot cause damage to it.

The method of inserting the IOL can now be described. First, the load chamber is placed in the fully open position. The IOL is laid lengthwise on the load chamber, so that the IOL will be folded along its length when the load chamber is folded. The load chamber is then folded, around the IOL, by grasping the flanges and bringing the flanges into abutting relation. Then the load chamber is inserted into the distal end of the injector portion, the flange of the load chamber fitting into the slot in the injector portion. Then, the insertion cone is threaded into the injector portion, and tightened, so that the beveled edge of the load chamber is in abutment with the corresponding surface inside the insertion cone, and so that there is one continuous lumen extending through the entire apparatus.

Although the above-described method is preferred, it is also possible, within the scope of the invention, to reverse the order of some of the steps. The folded load chamber can be inserted into the proximal end of the insertion cone, and the injector portion can then be fitted over the load chamber, and threaded onto the insertion cone.

Before the apparatus is inserted into the eye, it is desirable to flatten the distal tip of the insertion cone 38, as illustrated by reference numeral 63 in FIG. 3A. The flattening 63 permits the tip of the insertion cone to pass through the incision more easily. The tip can be molded to assume a flattened configuration, or it can be flattened manually, immediately before insertion of the IOL. The latter procedure is preferable, because the tip can be momentarily flattened, to fit easily into the incision, and still be resilient enough to expand, allowing easy passage for the lens and the plunger. Of course, it is within the scope of the invention to use a tip which is not flattened, as is shown in FIG. 3.

Before the apparatus is inserted into the incision, the plunger is advanced, pushing the IOL almost to the distal end of the insertion cone. Because the channels within the injector portion, the load chamber, and the insertion cone all define one continuous lumen, having a substantially constant diameter, the plunger can be pushed, without obstruction, through the entire insertion apparatus. The plunger is preferably marked so that the surgeon will know when the distal end of the plunger is about to reach the flattened portion of the insertion cone, or when the plunger is approaching the distal tip, in cases where the tip is not flattened. The distal tip is then inserted into the incision in the eye. The plunger is advanced further, causing the IOL to enter the eye. The length of the plunger is such that it does not extend beyond the distal tip of the insertion cone.

Due to the elasticity of the plastic used to construct the IOL, the IOL "flowers" out as it exits from the distal tip of the insertion cone. That is, the IOL gradually regains its original, non-folded orientation as it enters the eye. This "flowering out" is illustrated in FIG. 1, which shows most of the IOL having exited from the insertion cone. By the time the entire IOL has exited the insertion cone, the IOL will have returned to its original, unfolded shape. The insertion apparatus is then withdrawn, and the final position of the IOL may be adjusted by a small, bent needle, or other similar tool, inserted into the same incision.

It is preferable that the distal tip of the plunger 53 be constructed of a relatively soft material, such as rubber, or such as the material used to make non-linting surgical sponges, so that the IOL is not damaged by the plunger while the plunger is being advanced through the apparatus. It is also possible to use a plunger having a relatively hard tip, within the scope of this invention.

Because the insertion cone, load chamber, and injector portion are all separate pieces, in the embodiment described above, any or all of these components can be disposed of after one use. The components can all be made of molded plastic, or of any other suitable material or construction.

The IOL shown in FIG. 2 has webbed haptics 29, which, when the IOL is folded lengthwise, provide a resilient structure against which the plunger can push. However, there are other types of IOLs, having haptics which are mere loops. For example, such an IOL might have haptics which coincide with edge lines 31 of the IOL in FIG. 2. In the latter case, there is a danger that, when the plunger is advanced, the relatively flimsy haptic will be caught between the plunger and the wall of the injector portion. The embodiments shown in FIGS. 8 and 9 are designed to solve this problem, and are intended for use with looped haptics having no webbing.

In the embodiment of FIG. 8, the load chamber and the injector portion are formed of one piece, and the structure of the plunger is slightly modified. FIG. 8 shows load chamber 65 and injector portion 67 which are formed from the same piece of material. The load chamber and injector portion are separated along cut line 81, which extends through most, but not all, of the material, thereby permitting the load chamber to be opened, while still remaining attached to the injector portion. In FIG. 8, flanges 77 and 79 of load chamber 65 have been separated, and IOL 73 is also visible. Plunger 69, having handle 71, is equipped with a blunted hook 75 at its distal end, the hook extending through the loop defined by haptic 83 of the IOL. Plunger 69 also has threads 92 at its proximal end, for engagement with the injector portion.

FIG. 9 illustrates an embodiment wherein the load chamber, the injector portion, and the insertion cone are all formed of the same piece of material. The components of FIG. 9 which are identical to those shown in FIG. 8 are designated by similar reference numerals.

FIG. 9 depicts the load chamber 65 in the closed position, but it is understood that the plunger and the IOL have the same general structure as shown in FIG. 8. Cut lines 81 are plainly visible, as are flanges 77 and 79. The injector portion 67 is equipped with a cuff 90 which has a slot 92 for engagement of the flanges. Cuff 90 can be slid over the load chamber to hold the flanges in place.

When an IOL having a non-webbed haptic is used, the plunger is first advanced so that the hook 75 lies in the proximal end portion of the load chamber. Then the IOL is laid over the hook, so that the hook engages the loop. When the load chamber is then folded, and the plunger is advanced, the forward end of the hook will press against optic 85. The optic 85 is a relatively massive and resilient structure which can be pushed through its lumen, as is done in the first embodiment. Because the hook is inserted in the loop, the haptic will not be likely to interfere with the forward movement of the plunger.

In the embodiment of FIG. 8, the injector portion does not fit over the insertion cone, but the load chamber is connected to the insertion cone as before. In all of the embodiments, the injector portion, load chamber, and insertion cone still define a lumen for passage of the IOL, and the plunger, therethrough. In the embodiments of FIGS. 8 and 9, the components are preferably integrally formed, but it is also possible to form these components separately and to join them later.

It is understood that the embodiments of FIGS. 8 and 9 could also be used where the IOL has webbed haptics, and where no hook is needed on the distal end of the plunger. However, it is generally preferable to use the first-described embodiment, if possible, because its construction is more sturdy.

Regardless of the embodiment used, there are several different ways by which the plunger can be pushed through the injector portion. The simplest method is by hand. However, it is also possible to control the plunger remotely, such as with a cable, having a length of a few feet. In this manner, the plunger can be gradually advanced by a nurse, or other surgical assistant, at a distance from the patient, thereby minimizing interference with the surgery. Also, the motion of the plunger can be controlled by a motor. The motor generates rotational motion which can be converted, by a worm gear or similar device, into translational motion. The plunger can therefore be advanced at a precisely controlled, steady rate. The motor can be actuated by a foot switch, thereby allowing the operator of the motor the free use of both hands.

While the invention has been described with respect to the specific embodiments illustrated, it is understood that the invention can be modified in various ways. The precise structure of the load chamber can be varied somewhat; for example, its distal edge can be left unbeveled, or the bevel can assume different angles. The shape of the plunger, and the shape of the injector portion itself, can be changed, as long as the apparatus defines a continuous lumen sufficient for insertion of a folded IOL through the apparatus and into the eye. These and other modifications are to be deemed within the spirit and scope of the following claims.

What is claimed is:

1. Apparatus for inserting an intra-ocular lens into an eye, comprising:
    (a) a load chamber constructed of a flexible material, the load chamber having a pair of generally semi-cylindrical portions, both of the semi-cylindrical portions being connected to a flange, the load chamber being foldable, wherein the load chamber, in its folded position, defines a lumen for passage of the intra-ocular lens therethrough,
  (b) an insertion cone adapted to abut the load chamber, the insertion cone having a distal end adapted for insertion into a small incision in the eye, the insertion cone having a threaded portion at its proximal end, and
  (c) an injector portion, adapted to engage the threaded portion of the insertion cone, the injector portion comprising a generally cylindrical body having a central lumen therethrough, and having a slot, near its distal end, for engagement with the flanges of the folded load chamber, wherein the injector portion fits over the load chamber and onto the insertion cone, the injector portion including plunger means adapted for insertion through the lumen, the plunger means being of sufficient length to advance the lens through the load chamber, through the insertion cone, and into the eye.

2. The apparatus of claim 1, wherein the semi-cylindrical portions of the load chamber are flattened, wherein the flattened portions can be brought into abutment when the load chamber is in the unfolded position.

3. The apparatus of claim 2, the distal end of the load chamber being beveled, and the interior of the threaded portion of the insertion cone being similarly beveled, wherein the load chamber and the insertion cone can be brought into close abutment.

4. The apparatus of claim 3, wherein the distal end of the insertion cone is flattened, to conform generally to the shape of a small incision in the eye.

5. Apparatus for insertion of an intra-ocular lens into a small incision in an eye, comprising:
  (a) a load chamber, adapted to receive the intra-ocular lens, the load chamber being foldable about the lens, the folded load chamber defining a lumen for passage of the lens therethrough,
  (b) an insertion cone, adapted for receiving the load chamber, the insertion cone and the load chamber defining a lumen, having a substantially uniform diameter, for passage of the lens, the lumen defind by the insertion cone being contiguous with the lumen defined by the load chamber, and
  (c) an injector portion adapted to fit around the load chamber, the injector portion including means for pushing the lens through the folded load chamber, through the insertion cone, and through the incision into the eye.

6. The apparatus of claim 5, wherein the load chamber comprises a pair of semi-cylindrical members, the semi-cylindrical members together defining the lumen, when the load chamber is in its folded position, and a pair of flanges, attached to the semi-cylindrical members.

7. The apparatus of claim 6, wherein the injector portion comprises a generally cylindrical body, the injector portion having a slot which is keyed to the flanges of the load chamber, whereby the load chamber is adapted for insertion into, and generally rigid retention within, the injector portion.

8. The apparatus of claim 7, wherein the proximal end of the insertion cone has a threaded portion, and wherein the injector portion is adapted for threaded engagement with the insertion cone.

9. The apparatus of claim 8, wherein the distal end of the load chamber is beveled, and wherein the interior of the threaded portion of the insertion cone is similarly beveled, wherein the beveled portions of the load chamber and the insertion cone can be brought into close abutment.

10. The apparatus of claim 6, wherein the semi-cylindrical members have flattened portions, the flattened portions permitting the load chamber to be opened fully, with the flattened portions being in full abutment with each other.

11. A load chamber for insertion of an intra-ocular lens into an eye, comprising means defining a cylindrical member, the cylindrical member having a longitudinal opening and being longitudinally hinged, the cylindrical member having a pair of flanges connected to the cylindrical member and extending from the longitudinal opening, the flanges being non-parallel to the surface of the cylindrical member, at the point of connection, wherein the cylindrical member defines a lumen for the lens when the flanges are brought into abutment.

12. The load chamber of claim 11, wherein the cylindrical member is flattened at one side, the flattened portion permitting the complete opening of the load chamber around its hinge.

13. The load chamber of claim 12, wherein the load chamber has a distal end, the distal end being closest to the eye, and wherein the distal end of the load chamber is beveled.

14. In combination, a load chamber and an insertion cone for insertion of an intra-ocular lens into an eye, the load chamber comprising a flexible, hinged member, the load chamber defining a lumen for passage of the lens therethrough, the load chamber having at least one flange, the flange being connected to the hinged member and being non-parallel thereto at the point of connection, the insertion cone also defining a lumen for passage of the lens therethrough, the lumen of the insertion cone and the lumen of the load chamber being aligned to permit the passage of the lens through the load chamber and into the insertion cone, the lumen of the insertion cone and the lumen of the load chamber having a substantially uniform diameter, the load chamber being insertable into the insertion cone.

15. The combination of claim 14, further comprising means for advancing the folded intra-ocular lens through the lumen of the load chamber, through the lumen of the insertion cone, and into the eye.

16. A method for insertion of an intra-ocular lens into an eye, comprising the steps of:
  (a) placing the intra-ocular lens lengthwise along an unfolded flexible load chamber, the load chamber being foldable about the lens to define a lumen for the lens,
  (b) folding the load chamber about the lens,
  (c) inserting the load chamber into the distal end of an injector portion, the injector portion having a lumen which is contiguous with the lumen of the load chamber,
  (d) attaching the injector portion to the proximal end of an insertion cone, the insertion cone having a lumen which is contiguous with the lumen of the load chamber, the insertion cone being adapted for insertion of the lens into the eye, the lumen of the insertion cone and the lumen of the load chamber having a substantially uniform diameter for passage of the lens therethrough, (e) advancing a plunger through the lumen of the injector portion, through the lumen of the load chamber, and through the lumen of the insertion cone, so as to push the lens into the distal end of the insertion cone, (f) inserting the apparatus into an incision in the eye, and (g) advancing the plunger again, so as to push the lens out of the apparatus and into the eye.

17. The method of claim 16, wherein the first advancing step is preceded by the step of pinching the distal end of the insertion cone, so as to make the distal end conform generally to the shape of an incision in the eye.

18. The method of claim 16, wherein the folding step comprises the steps of grasping a pair of flanges provided on the load chamber, and bringing the flanges into abutment.

19. The method of claim 18, wherein the inserting step comprises the step of placing the flanges into a slot provided in the injector portion, wherein the load chamber is rigidly mounted within the injector portion.

20. Apparatus for insertion of an intra-ocular lens into a small incision in an eye, the intra-ocular lens having an optic portion and a looped haptic portion, comprising:

(a) a load chamber, adapted to receive the intra-ocular lens, the load chamber being foldable about the lens, the folded load chamber defining a lumen for passage of the lens therethrough, (b) an insertion cone, adapted for receiving the load chamber, the insertion cone defining a lumen for passage of the lens, the lumen being contiguous with the lumen defined by the load chamber, the lumen defined by the load chamber and the lumen defined by the insertion cone having a substantially uniform diameter, and (c) an injector portion connected to the load chamber, the injector portion including means for pushing the lens through the folded load chamber, through the insertion cone, and through the incision into the eye.

21. The apparatus of claim 20, wherein the load chamber and the injector portion are integrally formed.

22. The apparatus of claim 21, wherein the injector portion includes a hooked plunger means, adapted to fit through the haptic loop of the intra-ocular lens, wherein the plunger means is in abutting relation to the optic portion of the lens.

23. A method for insertion of an intra-ocular lens into an eye, the intra-ocular lens having an optic portion and a looped haptic portion, comprising the steps of:

(a) advancing a hooked plunger means through an injector portion and into an unfolded flexible load chamber attached to the injector portion, (b) placing the intra-ocular lens lengthwise along the unfolded load chamber, so that the hooked plunger engages the looped haptic, (c) folding the load chamber about the lens to define a lumen for the lens, (d) inserting the load chamber into an insertion cone, the insertion cone having a distal end portion, the insertion cone having a lumen contiguous with the lumen of the load chamber, the insertion cone being adapted for insertion of the lens into the eye, (e) advancing a plunger through the injector portion, through the lumen of the load chamber, and through the lumen of the insertion cone, so as to push the lens into the distal end portion of the insertion cone, (f) inserting the apparatus into the eye, and (g) advancing the plunger again, so as to push the lens out of the apparatus and into the eye.

24. Apparatus for insertion of an intra-ocular lens into a small incision in an eye, the intra-ocular lens having an optic portion and a looped haptic portion, the apparatus comprising a load chamber, an insertion cone, and an injector portion, wherein the load chamber, insertion cone and injector portion are connected together, wherein the load chamber is adapted to receive the intra-ocular lens, the load chamber being foldable about the lens, the folded lens chamber defining a lumen for passage of the lens therethrough, the insertion cone defining a lumen for passage of the lens, the lumen being contiguous with the lumen defined by the load chamber and having a substantially uniform diameter, wherein the injector portion includes means for pushing through the folded load chamber, through the insertion cone, and through the incision into the eye.

25. The apparatus of claim 24, wherein the load chamber has a pair of flanges, and wherein the apparatus further comprises a cuff adapted to be slid over the injector portion, the cuff having a slot which is snaped to engage the flanges of the load chamber.

26. Apparatus for insertion of an intra-ocular lens into a small incision in an eye, comprising:

(a) a load chamber, adapted to receive the intra-ocular lens, the load chamber being foldable about the lens, the folded load chamber defining a lumen for passage of the lens therethrough, (b) an insertion cone, adapted for receiving the load chamber, the insertion cone defining a lumen for passage of the lens, the lumen being contiguous with the lumen defined by the load chamber, and (c) an injector portion adapted to fit around the load chamber, the injector portion including means for pushing the lens through the folded load chamber, through the insertion cone, and through the incision into the eye, wherein the load chamber comprises a pair of semi-cylindrical members, the semi-cylindrical members together defining the lumen, when the load chamber is in its folded position, and a pair of flanges, attached to the semi-cylindrical members.

27. The apparatus of claim 26, wherein the injector portion comprises a generally cylindrical body, the injector portion having a slot which is keyed to the flanges of the load chamber, whereby the load chamber is adapted for insertion into, and generally rigid retention within, the injector portion.

28. The apparatus of claim 27, wherein the proximal end of the insertion cone has a threaded portion, and wherein the injector portion is adapted for threaded engagement with the insertion cone.

29. The apparatus of claim 28, wherein the distal end of the load chamber is beveled, and wherein the interior of the threaded portion of the insertion cone is similarly beveled, wherein the beveled portions of the load chamber and the insertion cone can be brought into close abutment.

30. The apparatus of claim 26, wherein the semi-cylindrical members have flattened portions, the flattened portions permitting the load chamber to be opened fully, with the flattened portions being in full abutment with each other.

31. A method for insertion of an intra-ocular lens into an eye, comprising the steps of:

(a) placing the intra-ocular lens lengthwise along an unfolded flexible load chamber, the load chamber being foldable about the lens to define a lumen for the lens, (b) folding the load chamber about the lens, (c) inserting the load chamber into the distal end of an injector portion, the injector portion having a lumen which is contiguous with the lumen of the load chamber, (d) attaching the injector portion to the proximal end of an insertion cone, the insertion cone having a lumen which is contiguous with the lumen of the load chamber, the insertion cone being adapted for insertion of the lens into the eye, (e) advancing a plunger through the lumen of the injector portion, through the lumen of the load chamber, and through the lumen of the insertion cone, so as to push the lens into the distal end of the insertion cone, (f) inserting the apparatus into an incision in the eye, and (g) advancing the plunger again, so as to push the lens out of the apparatus and into the eye, wherein the folding step comprises the steps of grasping a pair of flanges provided on the load chamber, and bringing the flanges into abutment.

32. The method of claim 31, wherein the inserting step comprises the step of placing the flanges into a slot provided in the injector portion, wherein the load chamber is ridigly mounted within the injector portion.

33. Apparatus for insertion of an intra-ocular lens into a small incision in an eye, the intra-ocular lens having an optic portion and a looped haptic portion, comprising:

(a) a load chamber, adapted to receive the intra-ocular lens, the load chamber being foldable about the lens, the folded load chamber defining a lumen for passage of the lens therethrough, (b) an insertion cone, adapted for receiving the load chamber, the insertion cone defining a lumen for passage of the lens, the lumen being contiguous with the lumen defined by the load chamber, and (c) an injector portion connected to the load chamber, the injector portion including means for pushing the lens through the folded load chamber, through the insertion cone, and through the incision into the eye, wherein the load chamber and the injector portion are integrally formed, and wherein the injector portion includes a hooked plunger means, adapted to fit through the haptic loop of the intra-ocular lens, wherein the plunger means is in abutting relation to the optic portion of the lens.

34. Apparatus for insertion of an intra-ocular lens into a small incision in an eye, the intra-ocular lens having an optic portion and a looped haptic portion, the apparatus comprising a load chamber, an insertion cone, and an injector portion, wherein the load chamber, insertion cone and injector portion are connected together, wherein the load chamber is adapted to receive the intra-ocular lens, the load chamber being foldable about the lens, the folded load chamber defining a lumen for passage of the lens therethrough, the insertion cone defining a lumen for passage of the lens, the lumen being contiguous with the lumen defined by the load chamber, wherein the injector portion includes means for pushing the lens through the folded load chamber, through the insertion cone, and through the incision into the eye, wherein the load chamber has a pair of flanges, and wherein the apparatus further comprises a cuff adapted to be slid over the injector portion, the cuff having a slot which is shaped to engage the flanges of the load chamber.

35. Apparatus for insertion of an intra-ocular lens into a small incision in an eye, the intra-ocular lens having an optic portion and a looped haptic portion, the apparatus comprising a load chamber, an insertion cone, and an injector portion, wherein the load chamber, insertion cone and injector portion are formed of one piece of material, wherein the load chamber is adapted to receive the intra-ocular lens, the load chamber being foldable about the lens, the folded load chamber defining a lumen for passage of the lens therethrough, the insertion cone defining a lumen for passage of the lens, the lumen being contiguous with the lumen defined by the load chamber, wherein the injector portion includes means for pushing the lens through the folded load chamber, through the insertion cone, and through the incision into the eye.

36. In combination, a load chamber and an insertion cone for insertion of an intra-ocular lens into an eye, the load chamber comprising a flexible, hinged member, the load chamber defining a lumen for passage of the lens therethrough, the insertion cone also defining a lumen for passage of the lens therethrough, the lumen of the insertion cone and the lumen of the load chamber being aligned to permit the passage of the lens through the load chamber and into the insertion cone, the lumen of the insertion cone and the lumen of the load chamber having a substantially uniform diameter, the load chamber being insertable into the insertion cone, and further comprising means for advancing the folded intra-ocular lens through the lumen of the load chamber, through the lumen of the insertion cone, and into the eye.

* * * * *